US009474594B2

(12) United States Patent
Schachar et al.

(10) Patent No.: US 9,474,594 B2
(45) Date of Patent: Oct. 25, 2016

(54) DEVICE AND METHOD FOR TREATMENT OF RETINAL DETACHMENT AND OTHER MALADIES OF THE EYE

(71) Applicants: Ira H. Schachar, La Jolla, CA (US); Ronald A. Schachar, La Jolla, CA (US)

(72) Inventors: Ira H. Schachar, La Jolla, CA (US); Ronald A. Schachar, La Jolla, CA (US)

( * ) Notice: Subject to any disclaimer, the term of this patent is extended or adjusted under 35 U.S.C. 154(b) by 160 days.

(21) Appl. No.: 13/772,762

(22) Filed: Feb. 21, 2013

(65) Prior Publication Data

US 2013/0218269 A1    Aug. 22, 2013

Related U.S. Application Data

(60) Provisional application No. 61/601,582, filed on Feb. 22, 2012.

(51) Int. Cl.
*A61F 2/14*    (2006.01)
*A61F 2/91*    (2013.01)
*A61F 9/007*   (2006.01)

(52) U.S. Cl.
CPC . *A61F 2/14* (2013.01); *A61F 2/91* (2013.01); *A61F 9/00727* (2013.01); *A61F 9/00781* (2013.01)

(58) Field of Classification Search
CPC ............ A61M 27/006; A61M 27/002; A61F 5/0079; A61F 5/0076; A61F 2/14; A61F 2/16; A61F 2/147
USPC ................................................ 623/4.1; 604/9
See application file for complete search history.

(56) References Cited

U.S. PATENT DOCUMENTS 4,299,227 A    11/1981    Lincoff
5,354,331 A    10/1994    Schachar
(Continued)

FOREIGN PATENT DOCUMENTS

WO    02/11648 A1    2/2002
WO    2009126464 A1    10/2009

OTHER PUBLICATIONS

International Search Report; Ser. No. PCT /US2013/027016; Jun. 26, 2013.
(Continued)

*Primary Examiner* — David H Willse
*Assistant Examiner* — Tiffany Shipmon
(74) *Attorney, Agent, or Firm* — Carlos R. Villamar; The Villamar Firm PLLC (57) ABSTRACT

The present invention relates generally to a device and method for the treatment of retinal detachment, ocular hypertension and glaucoma, and increasing the amplitude of accommodation. In an illustrative embodiment, the device includes a tapered, mesh tube. Once the device is within the sclera, the mesh expands to deform the sclera. When the device is placed within the posterior sclera for the treatment of a retinal tear, the device expands deforming the sclera so that the retinal pigment epithelium comes in contact with the retinal tear to seal the tear. For the treatment of ocular hypertension, glaucoma and to increase the amplitude of accommodation, the device is placed within the anterior sclera over the posterior plicata of the ciliary body, which upon expansion causes the underlying ciliary body to deform, resulting in traction on the trabecular meshwork and deformation of the ciliary body, which causes lowering of intraocular pressure, and increases the amplitude of accommodation in patients with ocular hypertension or decreased accommodation.

26 Claims, 4 Drawing Sheets

(56) References Cited

U.S. PATENT DOCUMENTS

| | | | |
|---|---|---|---|
| 5,366,474 A | 11/1994 | Blumenkanz et al. | |
| 5,465,737 A | 11/1995 | Schachar | |
| 5,489,299 A | 2/1996 | Schachar | |
| 5,503,165 A | 4/1996 | Schachar | |
| 5,529,076 A | 6/1996 | Schachar | |
| 5,722,952 A | 3/1998 | Schachar | |
| 6,007,578 A | 12/1999 | Schachar | |
| 6,197,056 B1 | 3/2001 | Schachar | |
| 6,280,468 B1 | 8/2001 | Schachar | |
| 6,299,640 B1 | 10/2001 | Schachar | |
| 6,547,714 B1 | 4/2003 | Dailey | |
| 7,927,372 B2 | 4/2011 | Griffis, III et al. | |
| 2002/0035397 A1 | 3/2002 | Baikoff | |
| 2002/0123804 A1* | 9/2002 | Gwon | A61F 2/147 623/4.1 |
| 2007/0293872 A1* | 12/2007 | Peyman | 606/107 |
| 2008/0228127 A1* | 9/2008 | Burns et al. | 604/9 |
| 2010/0010416 A1* | 1/2010 | Juan et al. | 604/9 |
| 2010/0191177 A1 | 7/2010 | Chang et al. | |

OTHER PUBLICATIONS

EP ISR and WO Ser. No. EP 13751893.2 dated Apr. 14, 2015.

* cited by examiner

The eye is anesthetized with application of a topical anesthetic and/or the injection of an anesthetic subconjunctivally, subtenons, or retrobulbarly. Alternatively, the procedure is performed under general anesthesia  502

The tip of the hypodermic needle is inserted through the conjunctiva or through an incision made in the conjunctivia  504

The tip of the needle is inserted perpendicularly into the sclera to 90% of the scleral thickness.  506

The needle is passed within the sclera and parallel to the scleral surface for 85% of the mesh tube's length while remaining at 90% of the scleral thickness. 508

The needle exits the sclera onto the surface of the sclera for the length of the tapered end of the mesh tube  510

The needle is retracted into the attached cylinder leaving the mesh tube within the sclera at 90% of the scleral thickness with its tapered ends on the surface of the sclera  512

The deformed posterior sclera causes the retinal pigment epithelium to come in contact with the retinal tear so that the tear is sealed, or deforms the anterior sclera causing deformation of the ciliary body with a resulting reduction in intraocular pressure and increasing the amplitude of accommodation.
514

FIG. 5

DEVICE AND METHOD FOR TREATMENT OF RETINAL DETACHMENT AND OTHER MALADIES OF THE EYE

CROSS REFERENCE TO RELATED DOCUMENTS

The present invention claims priority to U.S. Provisional Patent Application Ser. No. 61/601,582 of Ira H. SCHACHAR, entitled "DEVICE AND METHOD FOR TREATMENT OF RETINAL DETACHMENT AND OTHER MALADIES OF THE EYE," filed on Feb. 22, 2012, the entire disclosure of which is hereby incorporated by reference herein.

BACKGROUND OF THE INVENTION

1. Field of the Invention

The present invention relates generally to treating maladies of the eye, and more particularity to a device and method for the treatment of retinal detachment, ocular hypertension, glaucoma, and the like, and increasing the amplitude of accommodation by deformation of the sclera, and the like.

2. Discussion of the Background

Retinal detachment, ocular hypertension and reduction of the amplitude of accommodation are relatively common disorders that can lead to blindness, glaucoma and loss of the ability to read. However, conventional methods and devices for treatment of such disorders are still yet to be improved. Accordingly, there is a need for a device and method for the treatment of retinal detachment, ocular hypertension, glaucoma, and the like, and which can increase the amplitude of accommodation by deformation of the sclera, and the like.

SUMMARY OF THE INVENTION

The present invention disclosed herein includes an apparatus and method to treat retinal detachment, lower intraocular pressure and increase the amplitude of accommodation by controlled deformation of the sclera. The device of the present invention involves using a small bore hypodermic needle, typically 23 gauge or smaller, to insert a unique mesh tube into the sclera that once within the sclera expands to a predetermined size to ensure the magnitude of the scleral deformation is precisely predictable. The holes of the mesh prevent the device from dislodging from the sclera. The ends of the device are tapered and smooth to prevent any unwarranted damage to adjacent tissue. For the treatment of a retinal detachment, the device is placed intrasclerally in the posterior sclera under the retinal tear. The deformation of the posterior sclera brings the retinal pigment epithelium in contact with the retina to close the retinal tear. To reduce intraocular pressure or increase the amplitude of accommodation, the device is placed intrasclerally in the anterior sclera. The deformation of the sclera changes the shape of the ciliary body, which decreases aqueous humor production, improves aqueous humor outflow, and increases the force the ciliary muscle can apply. Advantageously, these changes in the configuration of the sclera and ciliary body lower intraocular pressure and increase the amplitude of accommodation.

Accordingly, it is an aspect of the present invention to use a mesh tube that can self expand to a predictable size within the sclera.

It is a further aspect of the present invention to use a mesh tube that has tapered smooth ends.

It is a further aspect of the present invention for a mesh tube to have unequal connecting points between struts of a mesh to prevent fracture of the mesh upon expansion.

It is a further aspect of the present invention to use a mesh tube made of titanium and nickel.

It is a further aspect of the present invention to use a mesh tube made of stainless steel that can be expanded to a predictable size within the sclera.

It is a further aspect of the present invention to use a balloon placed inside the mesh tube to expand the mesh tube with air or water pressure in order to control the size of expansion of the mesh tube within the sclera.

It is a further aspect of the present invention to use a plastic mesh tube that can self expand to a predictable size within the sclera.

It is a further aspect of the present invention to use a plastic mesh tube made of tightly woven polyester filaments.

It is a further aspect of the present invention to use a plastic mesh tube that does not biodegrade with time.

It is a further aspect of the present invention to use a plastic mesh tube that does biodegrade with time.

It is a further aspect of the present invention to place the mesh tube intrasclerally using a small 23 gauge hypodermic needle.

It is a further aspect of the present invention that the mesh tube in its unexpanded state can have an outer diameter of approximately 400 microns.

It is a further aspect of the present invention that the mesh tube can radially expand approximately 2.5 times once placed within the sclera.

It is a further aspect of the present invention for the mesh tube to partially protrude from within the sclera onto the intact surface of the sclera.

It is a further aspect of the present invention that the length of the mesh tube is approximately 6 mm in length when fully expanded.

It is a further aspect of the present invention that the first and second tapered ends of the mesh tube can be approximately 15% of the total length of the mesh tube.

It is a further aspect of the present invention that the mesh tube eludes a medication over time.

It is a further aspect of the present invention that the needle used to insert the mesh tube can be retracted so that the mesh tube can be properly placed within the sclera.

It is a further aspect of the present invention that the expandable mesh tube includes holes made by a laser and configured to maximize final expansion and rigidity and form a mesh pattern, the holes including one of diamond shaped holes, rectangular shaped holes, round shaped holes, elliptical shaped holes, and polygonal shaped holes.

It is a further aspect of the present invention that a total mass of material remaining in the expandable mesh tube is more or less than a mass removed by the laser in making the holes.

The foregoing has outlined rather broadly the features and technical advantages of the present invention so that those skilled in the art may better understand the detailed description of the invention that follows. Additional features and advantages of the invention will be described hereinafter that form the subject of the claims of the invention. Those skilled in the art should appreciate that they may readily use the conception and specific embodiment disclosed as a basis for modifying or designing other structures for carrying out the same purposes of the present invention. Those skilled in the art should also realize that such equivalent constructions do not depart from the spirit and scope of the invention in its broadest form.

Before undertaking the Detailed Description of the Invention below, it may be advantageous to set forth definitions of certain words and phrases used throughout this patent document: the terms "include" and "comprise" as well as derivatives thereof, mean inclusion without limitation; the term "or," is inclusive, meaning and/or; the phases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like. Definitions for certain words and phrases are provided throughout this patent document, those of ordinary skill in the art should understand that in many, if not most instances, such definitions apply to prior uses, as well as future uses, of such defined words and phrases.

BRIEF DESCRIPTION OF THE DRAWINGS

For a more complete understanding of the present invention and its advantages, reference is now made to the following description taken in conjunction with the accompanying drawings, in which like reference numerals represent like parts.

DETAILED DESCRIPTION OF THE INVENTION

The present invention includes recognition that retinal detachment, ocular hypertension and reduction of the amplitude of accommodation are relatively common disorders that can lead to blindness, glaucoma and loss of the ability to read. However, conventional methods and devices for treatment of such disorders are still yet to be improved. Retinal detachment generally occurs as a result of a tear in the retina. The retinal tear can be the consequence of trauma, vitreous traction, and the like. Retinal detachments are treated with scleral buckles that are sutured to the sclera, vitrectomy with laser photocoagulation and/or the placement of air and/or silicon oil into the vitreous cavity of the eye, cryotherapy, and/or diathermy. Each of these treatments has disadvantages. To seal the retinal hole, a scleral buckle, a silicone sponge, is sutured to the external scleral surface, which requires skill and is difficult to perform. The sutures are difficult to place in the sclera and can come loose. Vitrectomy is complex and puts the patient at risk for an intraocular infection. Cryotherapy and diathermy can damage more of the retina than is required to treat the retinal detachment.

Clearly there is a need for a device that can deform the sclera to seal the retinal tear that is simple to apply, is less invasive, placement can be precisely controlled, remains in place, does not require suturing and employs minimal surgical skill. Ocular hypertension is defined as elevated pressure within the eye that is above normal. Various topical and systemic medications are commonly used to lower intraocular pressure. These medications may have disadvantages. They require repetitive use and consequently, compliance is difficult and costly. Additionally, these medications have unwanted side effects, which may even be life threatening.

An alternate method to medication employs a laser to lower the intraocular pressure in the eye by increasing aqueous outflow. Laser energy is directed through the cornea at the trabecular meshwork (the site of aqueous outflow) or to the immediately adjacent tissue area to produce holes, which increase the volume of outflow. Multiple treatments are usually required because the benefit from these holes declines with time. These frequent treatments can cause pigment dispersion within the eye, which can block aqueous outflow and lead to an increase in intraocular pressure.

A further alternative method for reducing intraocular pressure involves making a surgical connection between the anterior chamber of the eye and the subconjunctival space. These methods include trabeculectomy to remove part of the trabecular meshwork through a partial thickness scleral flap to permit drainage of aqueous humor through the scleral flap into the subconjunctival space, or making a channel from the inner trabecular meshwork to Schlemn's canal or placing a tube between the anterior chamber and the subconjunctival or subcleral space. All of these methods have disadvantages. The surgical connection between the anterior chamber and the subconjunctival space can be too large causing excessive aqueous humor drainage resulting in hypotony and phthisis bulbi. The connection between the anterior chamber and the subconjunctival/subscleral space and/or Schlemn's canal can close from fibrosis with a return of increased intraocular pressure. The connection between the anterior chamber and the subconjunctival space offers potential access to bacteria, which can result in endophthalmitis with consequential loss of the eye. Furthermore, all these surgical techniques require significant surgical skill and can be complicated and cause intra and extraocular hemorrhage. The surgery can result in conjunctival belbs that can disturb the tear film resulting in dry eye and the conjunctival belb can be cosmetically displeasing.

Alternatively, ultrasound or a laser is used to destroy the pigmented epithelium of the pars plicata of the ciliary body to lower intraocular pressure. This procedure reduces aqueous production by destroying the site responsible for the production of aqueous humor. These procedures usually require multiple applications and can cause significant pigment dispersion, iris atrophy, sympathetic ophthalmia (an autoimmune reaction against the untreated eye), hypotony, and phthisis bulbi.

Clearly, there exists a need for a device that lowers intraocular pressure for extended periods of time with minimal side effects or heavy reliance on surgical skill. Accommodation is the ability of the eye to focus at near. The young, emmetropic eye can focus on objects ranging from approximately 7 cm (the near point) to infinity in less than a second. This action is regulated by the ciliary muscle, which, upon its contraction, induces an alteration in the shape of the crystalline lens of the eye. Unfortunately, this action becomes less effective with age resulting in a progressive decline in accommodative amplitude (making the near point more remote). This progressive decline in accommodative amplitude occurs at a linear rate time so that by the mid-forties, the near point has receded beyond the normal working distance. When this occurs, the patient has developed what is known as presbyopia, which progressively worsens until the late fifties when virtually no accommodation remains.

There are a number of current treatments for presbyopia. The most common are reading aids, which utilize bifocal, trifocal or multifocal lenses. These can take the form of either spectacles or contact lenses. In both cases, there are significant disadvantages. Reading aids can only be used at a finite number of focal distances, are difficult to use, restrict the visual field, and can decrease contrast sensitivity. In addition, contact lenses are difficult to wear due to an age-related change in the tear film.

Surgical options have also been explored to deal with the onset of presbyopia. Laser assisted keratomeleusis (LASIK) has been used to make the cornea multifocal, or to set one eye for near vision and the other eye for distance vision. Unfortunately, the former decreases contrast sensitivity and the latter prevents normal stereopsis. Multifocal or accommodating intraocular lenses have been used to replace the normal crystalline lenses of patients, but carry the potential complications of cataract surgery including retinal detachment and endophthalmitis.

A final surgical approach has been to expand the sclera to increase the effective working distance of the ciliary muscle to increase the accommodative amplitude. This has been achieved with both scleral incisions and implant surgery. These procedures have a number of disadvantages. Scleral incisions heal with time dramatically reducing their effect on accommodative amplitude. Implants can extrude with time or cause anterior-segment ischemia resulting in potential loss of the eye. Furthermore, the implants require significant surgical skill for proper placement, and even when placed correctly, changes in scleral elasticity can decrease their effect over time. Consequently, there is a need in the art for a device that can increase the amplitude of accommodation that is easy to place, less invasive, has minimal risk of extrusion, can remain in place for an extended period time with minimal side effects.

FIGS. 1-5, which are used to describe the various embodiments and principles of the present invention are by way of illustration and should not be construed in any way to limit the scope of the invention. Those skilled in the art will understand that the principles of the present invention may be implemented in any type of mesh tube that can expand within the sclera to deform the sclera. Table 1, below, lists the element numbers of FIGS. 1-4 and a description thereof.

TABLE 1

List of Element Numbers for FIGS. 1-4

Figure 1:
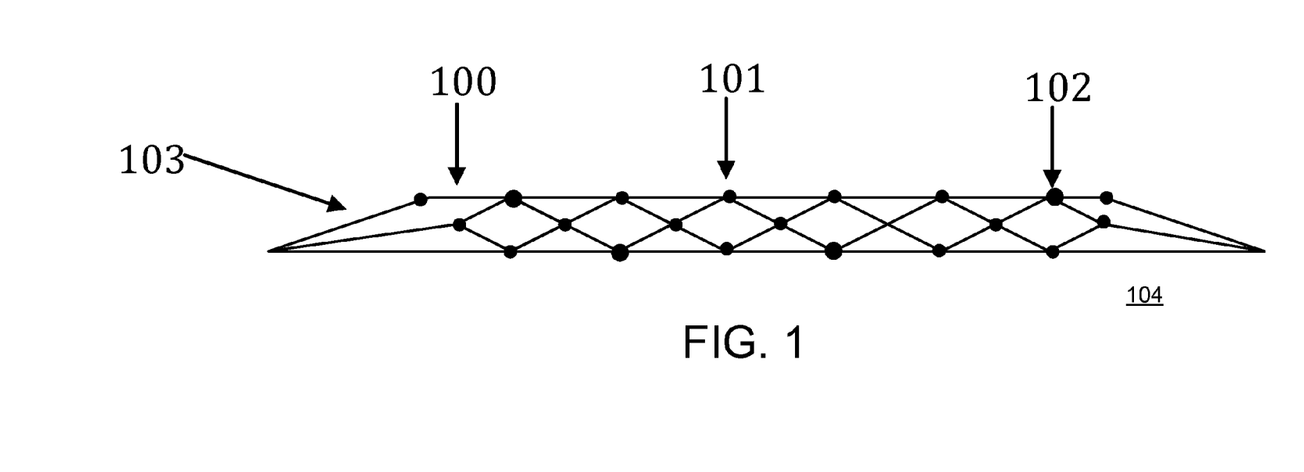
FIG. 1 illustrates a schematic diagram of an embodiment of a self-expanding mesh tube with tapered ends when fully expanded.
Figure 2:
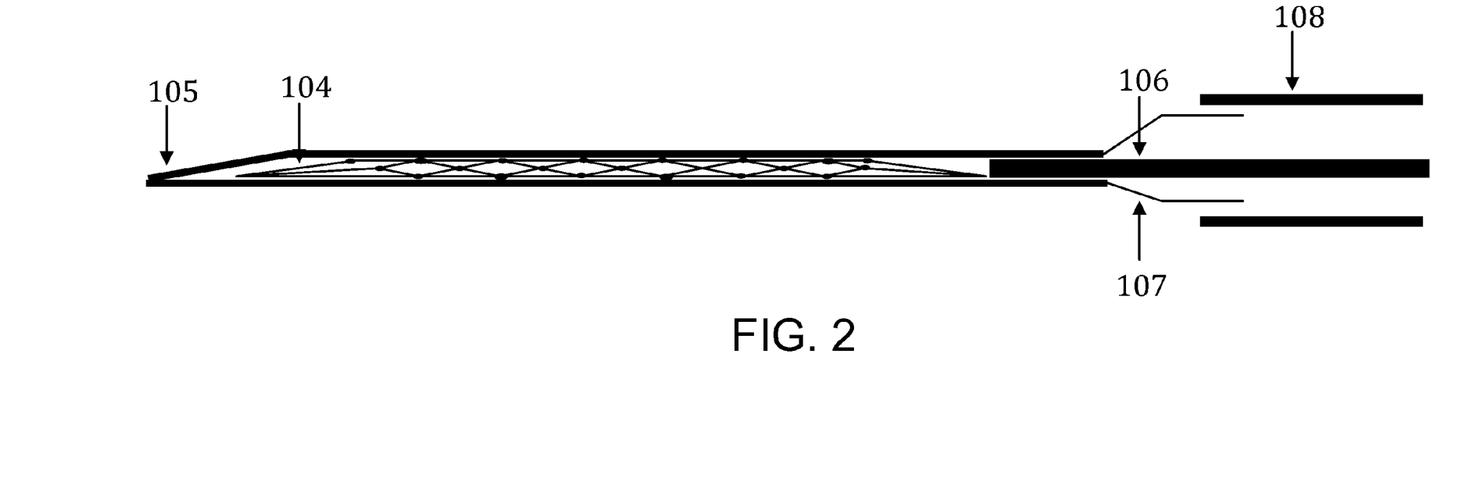
FIG. 2 illustrates a schematic diagram of an embodiment of a self expanding mesh tube with tapered ends before expansion while in a self retracting 23 gauge needle.
Figure 4:
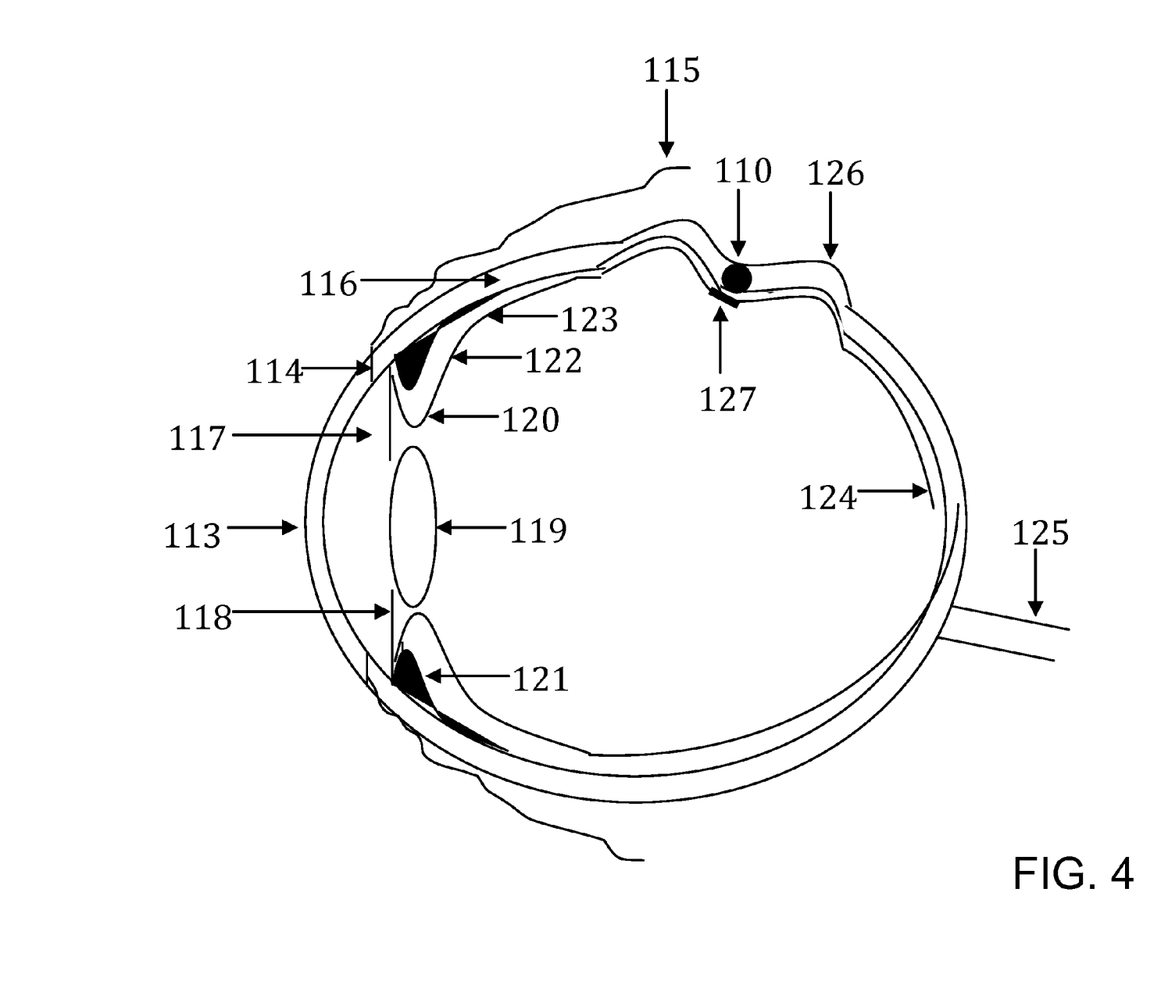
FIG. 4 illustrates a schematic diagram of an eye with an expanded mesh tube of the present invention within the posterior sclera, and with deformation of the sclera, and sealing of a retinal tear.

| | |
|---|---|
| FIG. 1 - expanded mesh tube | FIG. 4 - expanded mesh tube in the posterior sclera sealing a retinal tear |
| 100 - struts of mesh | 113 - cornea |
| 101 - connecting points | 114 - corneal-scleral limbus |
| 102 - different sized connecting points | 115 - conjunctiva |
| 103 - tapered ends | 116 - conjunctiva |
| FIG. 2 - unexpanded mesh tube within a retractable 23 gauge hypodermic needle | 117 - anterior chamber |
| 104 unexpanded mesh tube with tapered ends | 118 - iris |
| 105 - 23 gauge hypodermic needle | 119 - lens |
| 106 - stop within hypodermic needle | 120 - ciliary body |
| 107 - hub of hypodermic needle | 121 - ciliary muscle |

TABLE 1-continued

List of Element Numbers for FIGS. 1-4

Figure 3:
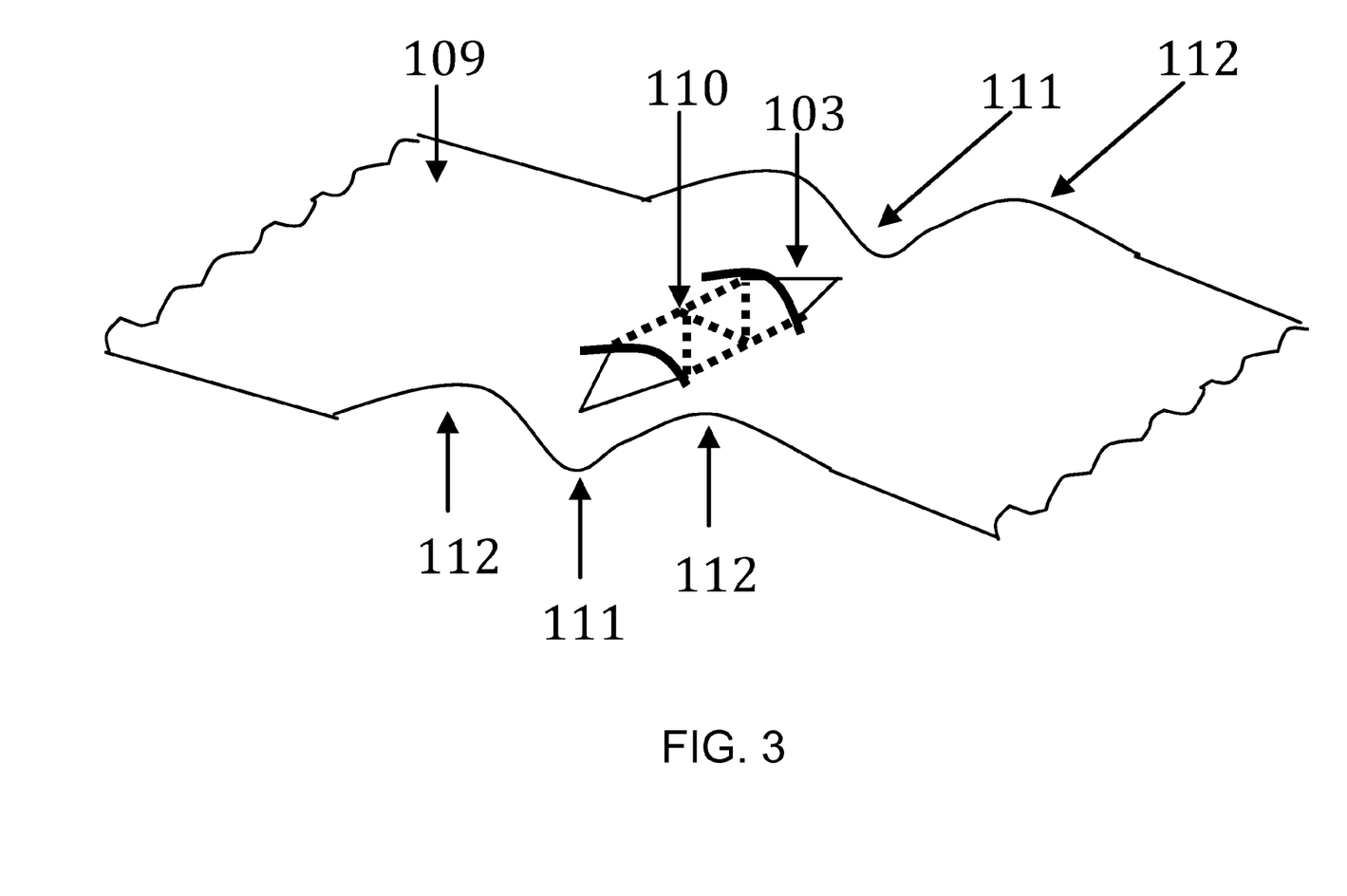
FIG. 3 illustrates a schematic diagram of an embodiment of a self-expanding mesh tube with tapered ends placed within the sclera for the treatment of a retinal detachment in accordance to the present invention.

| | |
|---|---|
| 108 - cylinder into which the hypodermic needle is retracted when the mesh tube is placed within the sclera | 122 - posterior portion of the pars plicata of the ciliary body |
| FIG. 3 - deformation of the scleral surface when the expanded mesh tube is within the sclera | 123 - pars plana |
| 109 - scleral surface | 124 - retina |
| 110 - expanded mesh tube | 125 - optic nerve |
| 111 - indentation of the sclera | 126 - deformation of posterior sclera |
| 112 - elevation of the sclera | 127 - sealed retinal tear |

FIG. 1 illustrates a schematic diagram of a device for the treatment of retinal detachment, ocular hypertension, glaucoma, and the like, and for increasing the amplitude of accommodation by deformation of the sclera, and the like, and which employs a self-expanding mesh tube 104. The mesh tube 104 has connecting struts 100, with connecting points 101, of different sizes 102, and tapered ends 103. In FIG. 1, a laser or any other suitable device can be used to make diamond shaped holes or holes of any suitable shape that can maximize final expansion, rigidity, and the like, to form a mesh pattern, and the like. For example, the mesh can be made of diamond shaped holes, rectangular shaped holes, round shaped holes, elliptical shaped holes, polygonal shaped holes, and the like. A total mass of the material remaining in the final mesh tube can be more or less than the mass that was removed by the laser to make the mesh, and the like.

FIG. 2. illustrates a schematic diagram of device of FIG. 1, when the unexpanded mesh tube 104 is within a retractable 23 gauge hypodermic needle 105, which has a stop 106 near its proximal end, so that the needle 105 along with its hub 107 can be retracted into a cylinder 108 to facilitate precise placement of the mesh tube 104 within the sclera.

FIG. 3 illustrates the surface of the sclera 109, when the mesh tube 104 in an expanded state 110 is inserted within the sclera 109 with its tapered ends 103 extending on the surface of the sclera 109 to cause indentation 111 and elevation 112 of the sclera 109.

FIG. 4. illustrates the eye with the cornea 113, corneal-scleral limbus 114, conjunctiva 115, sclera 116, anterior chamber 117, iris 118, lens 119, ciliary body 120, ciliary muscle 121, posterior portion of the pars plicata of the ciliary body 122, pars plana 123, retina 124, optic nerve 125, the expanded mesh tube 110 within the posterior sclera, with deformation of the sclera 126, and sealing of a retinal tear 127.

Thus, the present invention disclosed herein includes an apparatus and method to treat retinal detachment, lower intraocular pressure and increase the amplitude of accommodation by controlled deformation of the sclera.

The device of the present invention involves using a hypodermic needle with a small outer diameter having a range from 21 to 30 gauge. A hypodermic needle with a small outer diameter is employed because the thickness of the sclera ranges from 0.3 to 1.5 mm. In an illustrative embodiment, a 23 gauge hypodermic needle with an ultra thin wall is used to insert a unique mesh tube into the sclera. Once the mesh tube is within the sclera it expands to a predetermined size of 1.25 to 5 times its original diameter. In an illustrative embodiment, the mesh tube expands approximately 2 to 2.5 times its original diameter.

The mesh tube is made of materials that can expand when mechanical compression, temperature, or hydration is changed, such as titanium and nickel or an expandable plastic, and the like. Alternatively, a chemical reactant can be applied to expand the mesh or a pressurized water or air filled balloon placed within the mesh tube can be used to expand the mesh tube, as can be performed with a stainless steel mesh tube.

The original, unexpanded, diameters of the mesh tube have a range of 0.2 mm to 0.7 mm. In an illustrative embodiment, the original diameter is approximately 0.40 mm to facilitate insertion through an ultrathin walled 23 gauge hypodermic needle, and the like.

The magnitude of the scleral deformation is dependent on the expansion and stiffness of the tube and is enhanced when the first and second tapered ends of the mesh tube extend onto the surface of the sclera. The mesh tube can have a length from 2 mm to 15 mm with each tapered end having a length from 5% to 35% of the total length of the mesh tube. Shorter mesh tube lengths are preferred to avoid impinging on major scleral vessels such as the vortex veins or the anterior or posterior or short ciliary blood vessels. In an illustrative embodiment, the mesh tube has a length of 5 to 6 mm with each tapered end having a length of 15% of the total length of the mesh tube.

To maximize scleral deformation, the ends of the mesh tube extend onto the surface of the sclera. The first and second ends of the mesh tube are tapered to facilitate insertion, healing and removal of the mesh tube. In addition, the first and second ends are tapered and smooth to avoid damage and erosion of tissues that overlay the sclera, such as the conjunctiva or extraocular muscles.

The tapered ends may or may not expand when the body of the mesh tube expands within the sclera. In an illustrative embodiment, the first and second tapered ends expand as the body of the mesh tube expands. The horizontal level of the base the first and second tapered ends determine the magnitude of the scleral deformation. In an illustrative embodiment, when the first and second tapered ends expand, their bases (e.g., ends) stay below or within the same horizontal plane as the outer wall of the mesh tube.

The magnitude of the expansion of the end-width of the first and second tapered ends of the mesh tube determines the stability of the device once placed within the sclera. The range of expansion of the end-width of the first and second tapered ends is from 5% to 150% of the expanded diameter of the body of the mesh tube. In an illustrative embodiment, the expanded first and second tapered ends have end-widths close to the diameter of the expanded mesh tube of approximately 90% of the expanded diameter of the body of the mesh tube.

The mesh tube is made from biocompatible materials widely accepted by those skilled in the art such as titanium and nickel, stainless steel, expandable plastics, and the like, which may or may not be biodegradable.

To maximize scleral deformation the mesh tube should be relatively stiff in order to deform the sclera. In addition to the material properties and length of the mesh tube, the thickness of the struts and connecting points determine the stiffness of the expanded mesh tube. The thickness of the struts of the mesh tube can be from 1% to 90% of the original diameter of the mesh tube. In an illustrative embodiment, the struts have a thickness of approximately 25% of the thickness of the original diameter of the mesh tube. The spaces between the struts of the mesh assist in preventing the mesh tube from being inadvertently dislodged from the sclera.

The points connecting the struts may or may not have uniform thickness. In an illustrative embodiment, the points of connections of the body of the mesh tube near the beginning of the tapered ends and connecting points within the tapered ends are thicker than the connecting points of the rest of the mesh tube to prevent fracture of struts during expansion. The mesh tube can be made by using a laser to drill holes in a tube made of titanium and nickel, stainless steel or expandable plastic having an unexpanded outer diameter from 0.2 mm to 7 mm, and a wall thickness from 10% to 45% of the outer diameter of the unexpanded tube. In an illustrative embodiment, the tube is made of titanium and nickel with an unexpanded outer diameter of approximately 0.40 mm, and a wall thickness of approximately 25% of the unexpanded outer diameter of the tube. The holes are drilled through the wall of the tube to form the struts and connecting points.

The mesh tube may or may not be coated or impregnated within its structure with a medication (e.g., pharmaceutical or biologic) or several medications that can slowly elude over time. A collagen cross-linker for reinforcing the sclera to maintain and enhance the scleral deformation may be a medication eluded from the mesh tube.

The mesh tube may elude any of the following biological agents: antiproliferative agents, antineoplastic agents, antioxidants, endothelial cell growth factors, smooth muscle cell growth and/or migration inhibitors, thrombin inhibitors, immunosuppressive agents, anti-platelet aggregation agents, collagen synthesis inhibitors, therapeutic antibodies, nitric oxide donors, antisense oligonucleotides, wound healing agents, therapeutic gene transfer constructs, peptides, proteins, extracelluar matrix components, vasodialators, thrombolytics, anti-metabolites, growth factor agonists, antimitotics, steroids, steroidal antiinflammatory agents, chemokines, proliferator-activated receptor-gamma agonists, proliferator-activated receptor-alpha agonists, proliferator-activated receptor-beta agonists, proliferator-activated receptor-alpha/beta agonists, proliferator-activated receptor-delta agonists, NF.kappa.beta., proliferator-activated receptor-alpha-gamma agonists, nonsterodial antiinflammatory agents, angiotensin converting enzyme (ACE) inhibitors, free radical scavengers, inhibitors of the CX3CR1 receptor, small interfering RNAs, and anti-cancer chemotherapeutic agents, and/or have anti-inflammatory, anti-infective, anti-angiogenic, ocular hypotensive, anti-carcinogenic, anti-growth, anti-immunologic, anti-lipid and/or a fluid reducing properties, and the like.

The mesh tube may elude any of the following pharmaceutical agents: anti-inflammatory agents, anti-infective agents, anti-angiogenic agents, ocular hypotensive agents, anti-carcinogenic agents, anti-growth agents, anti-immunologic agents, anti-lipid agents, kallikrien inhibitors, fluid reducing agents, cyclosporin A, mycophenolic acid, mycophenolate mofetil acid, rapamycin, rapamycin derivatives, biolimus A9, CCI-779, RAD 001, AP23573, azathioprene, pimecrolimus, tacrolimus (FK506), tranilast, dexamethasone, corticosteroid, everolimus, retinoic acid, vitamin E, rosglitazone, simvastatins, fluvastatin, estrogen, 17.beta.-estradiol, hydrocortisone, acetaminophen, ibuprofen, naproxen, fluticasone, clobetasol, adalimumab, sulindac, dihydroepiandrosterone, testosterone, puerarin, platelet factor 4, basic fibroblast growth factor, fibronectin, butyric acid, butyric acid derivatives, paclitaxel, paclitaxel derivatives, LBM-642, deforolimus, and probucol, and the like.

The method of manufacture of the mesh tube determines the magnitude of the expansion and stiffness of the mesh tube to precisely predict the amount of scleral deformation. For the treatment of a retinal detachment, the device is placed intrasclerally in the posterior sclera under the retinal tear. The deformation of the posterior sclera brings the retinal pigment epithelium in contact with the retina to close the retinal tear.

To reduce intraocular pressure or increase the amplitude of accommodation the device is placed intrasclerally in the anterior sclera. In an illustrative embodiment, the mesh tube is placed over the posterior portion of the pars plicata of the ciliary body. The deformation of the sclera changes the shape of the ciliary body, which decreases aqueous humor production, improves aqueous humor outflow and increases the force the ciliary muscle can apply. These changes in the configuration of the sclera and ciliary body lower intraocular pressure and increase the amplitude of accommodation.

Figure 5:
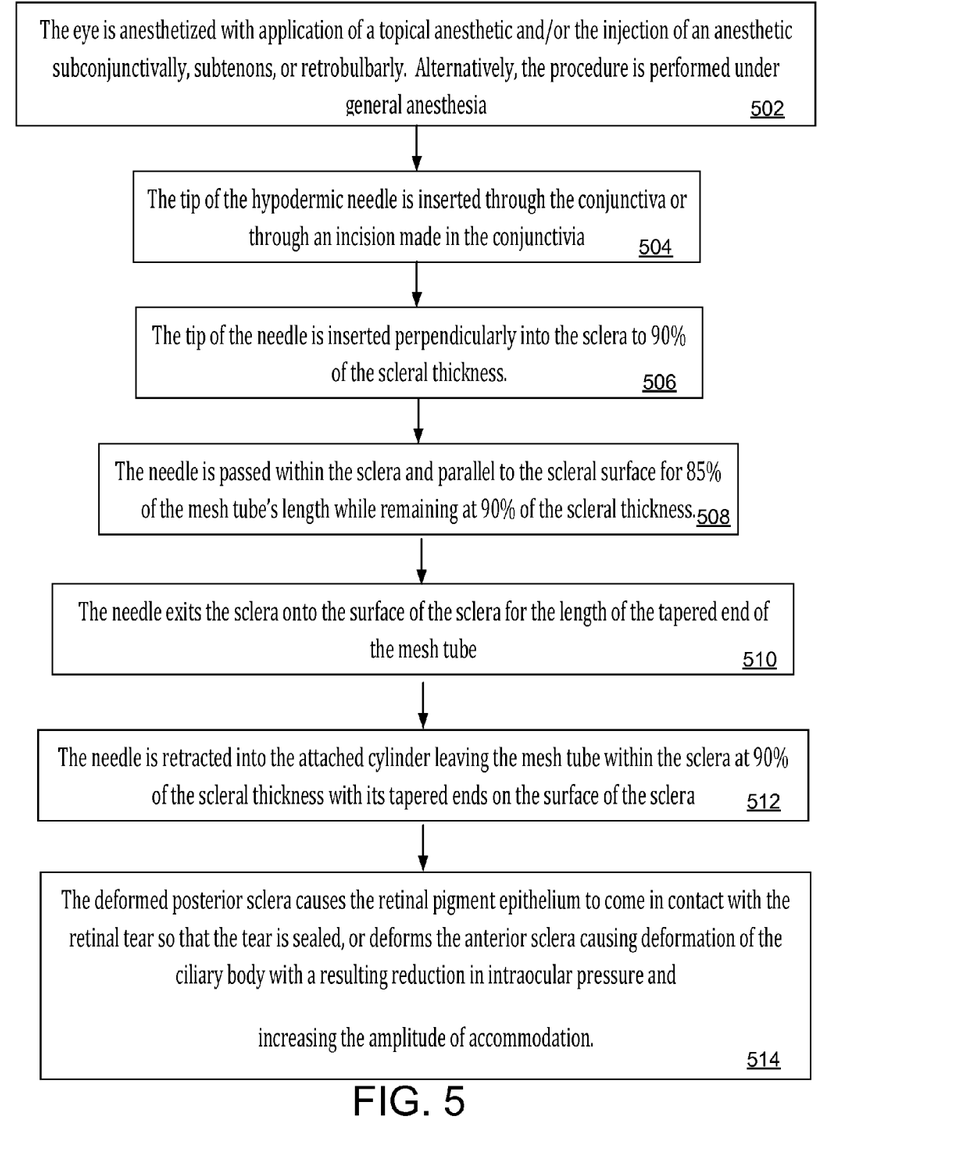
FIG. 5 is a flow diagram of an embodiment using a self-expanding mesh tube with tapered ends in accordance with the present invention.

FIG. 5 is a flow diagram of an embodiment using a self-expanding mesh tube with tapered ends in accordance with the present invention of FIGS. 1-4. In FIG. 5, at step 502, the eye is anesthetized with application of a topical anesthetic and/or the injection of an anesthetic subconjunctivally, subtenons, or retrobulbarly, and the like. Alternatively, the procedure is performed under general anesthesia. At step 504, the tip of the hypodermic needle is inserted through the conjunctiva or through an incision made in the conjunctivia. At step 506, the tip of the needle is inserted perpendicularly into the sclera to 90% of the scleral thickness. At step 508, the needle is passed within the sclera and parallel to the scleral surface for 85% of the mesh tube's length while remaining at 90% of the scleral thickness. At step 510, the needle exits the sclera onto the surface of the sclera for the length of the tapered end of the mesh tube. At step 512, the needle is retracted into the attached cylinder leaving the mesh tube within the sclera at 90% of the scleral thickness with its tapered ends on the surface of the sclera. At step 514, the deformed posterior sclera causes the retinal pigment epithelium to come in contact with the retinal tear so that the tear is sealed, or deforms the anterior sclera causing deformation of the ciliary body with a resulting reduction in intraocular pressure and increasing the amplitude of accommodation, completing the procedure.

While the present invention have been described in connection with a number of illustrative embodiments and implementations, the present invention is not so limited, but rather covers various modifications and equivalent arrangements, which fall within the purview of the appended claims.

What is claimed is:

1. A device for effecting deformation of a sclera of an eye, the device comprising:
    an expandable, mesh tube having holes dispersed through an entire surface thereof and with first and second tapered ends,
    wherein the mesh tube is configured to be inserted into a sclera of an eye in an unexpanded state and deform the sclera in an expanded state,
    a central portion of the mesh tube is intrascleral and the first and second tapered ends are each external to the sclera on top of an intact scleral surface in order to deform the sclera due to the expansion by the mesh tube from the unexpanded state to the expanded state, and
    the mesh tube in the expanded state simultaneously causes the sclera to be deformed so that the sclera moves towards the inside of the eye while simultaneously causing the sclera to move towards the outside of the eye,
    wherein the mesh tube includes struts,
    connecting points of the struts are of different sizes, and the first and second tapered ends and the connecting points within the tapered ends are thicker than the connecting points of the mesh tube.

2. The device of claim 1, wherein a base of the first and second tapered ends of the mesh tube lie in a same horizontal plane as an outer diameter of the mesh tube when the mesh tube is in the expanded state.

3. The device of claim 1, wherein a base of the first and second tapered ends of the mesh tube lie in a plane below a horizontal plane of an outer diameter of the mesh tube when the mesh tube is in the expanded state.

4. The device of claim 1, wherein the mesh tube is made of biocompatible titanium and nickel, stainless steel or an expandable plastic that is or is not biodegradable.

5. The device of claim 1, wherein the struts have a thickness from 15 to 90% of an unexpanded diameter of the mesh tube.

6. The device of claim 5, wherein the struts have an approximate thickness of 25% of an unexpanded diameter of the mesh tube.

7. The device of claim 1, wherein the mesh tube has an unexpanded diameter from 0.2 mm to 0.7 mm.

8. The device of claim 1, wherein the mesh tube has an unexpanded diameter of approximately 0.4 mm.

9. The device of claim 1, wherein a wall thickness of a tube from which the mesh tube is made is 0% to 45% of an outer unexpanded diameter of the mesh tube.

10. The device of claim 1, wherein a wall thickness of a tube from which the mesh tube is made has is approximately 25% of an outer unexpanded diameter of the mesh tube.

11. The device of claim 1, wherein the mesh tube is approximately 2 mm to 15 mm in length.

12. The device of claim 1, wherein the mesh tube is approximately 5 to 6 mm in length.

13. The device of claim 1, wherein the first and second tapered ends of the mesh tube each have a length of approximately 5% to 35% of a total length of the mesh tube.

14. The device of claim 1, wherein the first and second tapered ends of the mesh tube each have a length of approximately 15% of a total length of the mesh tube.

15. The device of claim 1, wherein the first and second tapered ends of the mesh tube do not expand with expansion of a body of the mesh tube.

16. The device of claim 1, wherein end-widths of the first and second tapered ends of the mesh tube expand from 5% to 150% of an expanded body of the mesh tube.

17. The device of claim 1, wherein end-widths of the first and second tapered ends of the mesh tube expand approximately to 90% of an expanded body of the mesh tube.

18. The device of claim 1, wherein the device is inserted into a sclera through a 21 gauge to a 30 gauge hypodermic needle.

19. The device of claim 1, wherein the device is inserted into a sclera through a 23 gauge hypodermic needle.

20. The device of claim 1, wherein the device is inserted into a sclera through a hypodermic needle that is retractable and includes a stop.

21. The device of claim 1, wherein the device is coated or impregnated with a biological agent that eludes from the mesh tube over time.

22. The device of claim 1, wherein the device is coated or impregnated with a pharmaceutical agent that eludes from the mesh tube over time.

23. The device of claim 1, wherein the device is coated or impregnated with a collagen cross-linking agent that eludes from the mesh tube over time.

24. The device of claim 1, wherein the expandable mesh tube includes holes made by a laser and configured to maximize final expansion and rigidity and form a mesh pattern, the holes including one of diamond shaped holes, rectangular shaped holes, round shaped holes, elliptical shaped holes, and polygonal shaped holes.

25. The device of claim 24, wherein a total mass of material remaining in the expandable mesh tube is more than a mass removed by the laser in making the holes.

26. The device of claim 24, wherein a total mass of material remaining in the expandable mesh tube is less than a mass removed by the laser in making the holes.

* * * * *